United States Patent [19]

Carter

[11] Patent Number: 5,780,594
[45] Date of Patent: Jul. 14, 1998

[54] BIOLOGICALLY ACTIVE PROTEIN FRAGMENTS CONTAINING SPECIFIC BINDING REGIONS OF SERUM ALBUMIN OR RELATED PROTEINS

[75] Inventor: Daniel C. Carter, Huntsville, Ala.

[73] Assignee: The United States of America as represented by the Administrator of the National Aeronautics and Space Administration, Washington, D.C.

[21] Appl. No.: 448,196

[22] Filed: May 23, 1995

Related U.S. Application Data

[63] Continuation of Ser. No. 24,547, Mar. 1, 1993, abandoned.
[51] Int. Cl.⁶ .................................................. C07K 14/76
[52] U.S. Cl. .................. 530/363; 530/350; 435/69.1; 435/252.3; 435/320.1
[58] Field of Search ..................... 435/69.1, 252.3, 435/320.1; 530/350, 363

[56] References Cited

PUBLICATIONS

He et al "Atomic Structure and Chemistry ... " Nature 358 pp. 209–215, Jul. 16, 1992.
Carter et al "Three Dimensional Structure ... " Science 244 pp. 1195–1198, Jun. 9, 1989.
Hirayama et al. "Rapid Confirmation and Revision ... " Biochem Biophys. Res. Comm. vol. 173, No. 2 pp. 639–646 Dec. 14, 1990.
Hamilton et al. (1991) Locations of the Three Primary Binding Sites for Long–Chain Fatty Acids on Bovine Serum Albumin. Proc. Natl. Acad. Sci. USA. vol.88, pp. 2051–2054.
Johanson et al. (1981) Refolding of Bovine Serum Albumin and Its Proteolytic Fragments. J. Biol. Chem. vol. 256, No. 1, pp. 445–450.
Carter et al., "Structure of human serum albumin", Science, vol. 249, pp. 302–303, Jul. 20, 1990.
NASA, Tech Briefs, Mar. 1992, p. 94, Author: Daniel C. Carter, Sequences of Amino Acids for Human Serum Albumin.

Primary Examiner—Robert A. Wax
Assistant Examiner—Enrique D. Longton
Attorney, Agent, or Firm—Robert L. Broad, Jr.

[57] ABSTRACT

In accordance with the present invention, biologically active protein fragments can be constructed which contain only those specific portions of the serum albumin family of proteins such as regions known as subdomains IIA and IIIA which are primarily responsible for the binding properties of the serum albumins. The artificial serums that can be prepared from these biologically active protein fragments are advantageous in that they can be produced much more easily than serums containing the whole albumin, yet still retain all or most of the original binding potential of the full albumin proteins. In addition, since the protein fragment serums of the present invention can be made from non-natural sources using conventional recombinant DNA techniques, they are far safer than serums containing natural albumin because they do not carry the potentially harmful viruses and other contaminants that will be found in the natural substances.

11 Claims, 4 Drawing Sheets

```
          ┌─h1(I)─┐    ┌──h2(I)───┐        ┌───h3(I)────┐
1         │    11 │    │ 21       │ 31     │   41       │ 51
DAHKSEVAHR  FKDLGEENFK  ALVLIAFAQY  LQQCPFEDHV  KLVNEVTEFA  KTCVADESAE
DTHKSEIAHR  FKDLGEEHFK  GLVLIAFSQY  LQQCPFDEHV  KLVNELTEFA  KTCVADESHA
DTHKSEIAHR  FNDLGEKHFK  GLVLVAFSQY  LQQCPFEDHV  KLVNEVTEFA  KKCAADESAE
DTHKSEIAHR  FNDLGEENFQ  GLVLIAFSQY  LQQCPFEDHV  KLVKELTEFA  KTCVADESHA
EAHKSEIAHR  FKDLGEQHFK  GLVLIAFSQY  LQKCPYEEHI  KLVQEVTDFA  KTCVADENAE
VDHHKHIADM  YNLLTERTFK  GLTLAIVSQN  LQKCSLEELS  KLVNEINDFA  KSCTGNDKTP
SQAQNQICTI  FTEAKEDGFK  SLILVGLAQN  LPDSTLGDLV  PLIAEALAMG  VKCCSDTPPE

┌──h4(I)───┐          ┌─h5(I)┐  ┌─h6(I)─┐
61        │    71    │ 81       │  91 │  │  101  │ 111         │
NCDKSLHTLF  GDKLCTVATL  RETYGEMADC  CAKQEPERNE  CFLQHKDDNP  NLPRLVRPEV
GCEKSLHTLF  GDELCKVASL  RETYGDMADC  CEKQEPERNE  CFLSHKDDSP  DLPKL*KPDP
NCDKSLHTLF  GDKLCTVATL  RATYGELADC  CEKQEPERNE  CFLTHKDDHP  NLPKL*KPEP
GCDKSLHTLF  GDELCKVATL  RETYGDMADC  CEKQEPERNE  CFLNHKDDSP  DLPKL*KPEP
NCDKSIHTLF  GDKLCAIPKL  RDNYGELADC  CAKQEPERNE  CFLQHKDDNP  NLPPFQRPEA
ECEKPIGTLF  YDKLCADPKV  GVNYEWSKEC  CSKQDPERAQ  CFRAHRVFEH  N*P**VRPKP
DCERDVADLF  QSAVCSSETL  VEKN*DLKMC  CEKTAAERTH  CFVDHKAKIP  RDLSLKAELPA h7(I)┐    ┌───h8(I)───┐          ┌────h9(I)────┐
121  │    │ 131       │ 141  │  151       │ 161       │ 171     │
DVMCTAFHDN  EETFLKKYLY  EIARRHPYFY  APELLFFAKR  YKAAFTECCQ  AADKAACLLP
NTLCDEFKAD  EKKFWGKYLY  EIARRHPYFY  APELLYYANK  YNGVFQECCQ  AEDKGACLLP
DAQCAAFQED  PDKFLGKYLY  EVARRHPYFY  GPELLFHAEE  YKADFTECCP  ADDKLACLIP
DTLCAEFKAD  EKKFWGKYLY  EVARRHPYFY  APELLYYANK  YNGVFQECCQ  AEDKGACLLP
EAMCTSFQEN  PTSFLGHYLH  EVARRHPYFY  APELLYYAEK  YNEVLTQCCT  ESDKAACLTP
EETCALFKEH  PDDLLSAFIH  EEARNHPDLY  PPAVLLLTQQ  YGKLVEHCCE  EEDKDKCFAE
ADQCEDFKKD  HKAFVGRFIF  KFSKSNPMLP  PHVVLAIAKG  YGEVLTTCCG  EAEAQTCFDT

──────h10(I)── h1(II)─┐         ┌────h2(II)────┐       ┌─h3(II)─┐
181       │  201    │ 211       │ 221      │ 231      │
KLDELRDEGK  ASSAKQRLKC  ASLQKFGERA  FKAWAVARLS  QRFPKAEFAE  VSKLVTDLTK
KIETMREKVL  ASSARQRLRC  ASIQKFGERA  LKAWSVARLS  QKFPKAEFVE  VTKLVTDLTK
KLDALKERIL  LSSAKERLKC  SSFQNFGERA  VKAWSVARLS  QKFPKADFAE  VSKIVTDLTK
KIDAMREKVL  ASSARQRLRC  ASIQKFGERA  LKAWSVARLS  QKFPKADFTD  VTKIVTDLTK
KLDAVKEKAL  VAAVRQMKC   SSMQRFGERA  FKAWAVARMS  QRFPNAEFAE  ITKLATDVTK
KMKELMKHSH  SIEDKQKHFC  WIVNNYPERV  IKALNLARVS  HRYPKPDFKL  AHKFTEETTH
KKATFQHAVM  KRVAELRSLC  IVHKKYGDRV  VKAKKLVQYS  QKMPQASFQE  MGGMVDKIVA
```

*FIG. 2-1*

```
         ┌───h4(II)────────┐         ┌h5(II)┐    ┌h6(II)┐
┌──241──┐ ┌──251    261───┐   271       281        291
VHTECCHGDL LECADDRADL AKYICENQDS ISS KLKECCE KPLLEKSHCI AEVENDEMPA
VHKECCHGDL LECADDRADL AKYICDNQDT ISS KLKECCD KPLLEKSHCI AEVEKDAIPE
VHKECCHGDL LECADDRADL AKYICEHQDS ISG KLKACCD KPLLQKSHCI AEVKEDDLPS
VHKECCHGDL LECADDRADL AKYICDHQDA LSS KLKECCD KPVLEKSHCI AEVDKDAVPE
INKECCHGDL LECADDRAEL AKYMCENQAT ISS KLQACCD KPVLQKSQCL AETEHDNIPA
FIKDCCHGDM FECMTERLEL SEHTCQHKDE LST KLEKCCN LPLLERTYCI VTLENDDVPA
TVAPCCSGDM VTCMKERKTL VDEVCADESV LSRAAGLSACCK EDAVHRGSCV EAMKPDPKPD

┌h7(II)┐ ┌──h8(II)──┐                 ┌──────h9(II)──────
   301         311  │  321│     331    │  341         351
DLPSLAADFV ESKDVCKNYA EAKDVFLGMF LYEYARRHPD YSVVLLLRLA KTYETTLEKC
NLPPLTADFA EDKDVCKNYQ EAKDAFLGSF LYEYSRRHPE YAVSVLLRLA KEYEATLEEC
DIPALAADFA EDKEICKHYK DAKDVFLGTF LYEYSRRHPD YSVSLLLRIA KTYEATLEKC
NLPPLTADFA EDKEVCKNYQ EAKDVFLGSF LYEYSRRHPE YAVSVLLRLA KEYEATLEDC
DLPSIAADFV EDKEVCKNYA EAKDVFLGTF LYEYSRRHPD YSVSLLLRLA KKYEATLEKC
ELSKPITEFT EDPHVCEKYA ENKS*FL*EI SPWQSQETPE LSEQFLLQSA KEYESLLNKC
GLSEHYDIHA DIAAVCQTFT KTPDVAMGKL VYEISVRHPE SSQQVILRFA KEAEQALLQC

┐       ┌─────── h10(II)─h1(III) ──────┐         ┌─h2(III)─┐
361     │    371        381        391  │  401    411   │
CAAHDPHECY AKVFD    EFKPL  VEEPQNLIKQ NCELFKQLGE YKFQNALLVR YTKKVPQVST
CAKDDPHACY STVFD    KLKHL  VDEPQNLIKQ NCDQFEKLGE YGFQNALIVR YTRKVPQVST
CAEADPPACY RTVFD    QFTPL  VEEPKSLVKK NCDLFEEVGE YDFQNALIVR YTKKAPQVST
CAKEDPHACY ATVFD    KLKHL  VDEPQNLIKK NCELFEKHGE YGFQNALIVR YTRKAPQVST
CAEGDPPACY GTVLA    EFQPL  VEEPKNLVKT NCELYEKLGE YGFQNAVLVR YTQKAPQVST
CFSDNPPECY KDGAD    RFMNE  AKERFAYLKQ NCDILHEHGE YLFENELLIR YTKKMPQVSD
CDMEDHAECV KTALAGSDIDKKI  TDETD*YYKK MCAAEEAAVSD DSFEKSMMVY YTRIMPQASF

┌───── h3(III)──────┐         ┌────── h4(III) ──────┐        ┌h5(III)┐
391         431        441         451         461         471
PTLVEVSRNL GKVGSKCCKH PEAKRMPCAE DYLSVVLNQL CVLHEKTPVS DRVTKCCTES
PTLVEVSRSL GKVGTRCCTK PESERMPCTE DYLSLILNRL CVLHEKTPVS EKVTKCCTES
PTLVEIGRTL GKVGSRCCKL PESERLPCSE NHLALALNRL CVLHEKTPVS EKITKCCTDS
PTLVEISRSL GKVGTKCCAK PESERMPCTE DYLSLILNRL CVLHEKTPVS EKVTKCCTES
PTLVEAARNL GRVGTKCCTL PEAQRLPCVE DYLSAILNRL CVLHEKTPVS EKVTKCCSGS
ETLIGIAHQM ADIGEHCCAV PENQRMPCAE GDLTILIGKM CERQKKTFIN NHVAHCCTDS
DQLHMVSETV HDVLHACCKD EQGHFVLPCAE EKLTDAIDAT CDDYDPSSIN PHIAHCCNQS
```

FIG. 2-2

```
       ┌─h6(III)─┐                          ┌─h7(III)─┐┌──h8(III)──┐
  481 │          491          501          511 │       │ 521          531 │
  LVNRRPCFSA   LEVDETYVPK   EFNAETFTFH   ADICTLSEKE   RQIKKQTALV   ELVKHKPKAT
  LVNRRPCFSA   LTPDETYVPK   AFDEKLFTFH   ADICTLPDTE   KQIKKQTALV   ELLKHKPKAT
  LAERRPCFSA   LELDEGYVPK   EFKAETFTFH   ADICTLPEDE   KQIKKQSALA   ELVKHKPKAT
  LVNRRPCFSD   LTLDETYVPK   PFDEKFFTFH   ADICTLPDTE   KQIKKQTALV   ELLKHKPKAT
  LVERRPCFSA   LTVDETYVPK   EFKAETFTFH   SDICTLPDKE   KQIKKQTALA   ELVKHKPKAT
  YSGMRSCFTA   LGPDEDYVPP   PVTDDTFHFD   DKICTANDKE   KQHIKQKFLV   KLIKVSPKLE
  YSMRRHCILA   IQPDTEFTPP   ELDASSFHMG   PELCTKDSKD   LLLSGKKLLY   GVVRHKTTIT
       ┌─h9(III)─┐          ┌──h10(III)──────────────────┐
  541 │          551 │      561 │        571           581 │
  KEQLKAVMDD   FAAFVEKCCK   ADDKETCFAE   EGKKLVAASQ   AALGL
  EEQLKTVMEN   FVAFVDKCCA   ADDKEACFAV   EGPKLVVSTQ   TALA*
  KEQLKTVLGN   FSAFVAKCCG   REDKEACFAE   EGPKLVASSQ   LALA*
  DEQLKTVMEN   FVAFVDKCCA   ADDKEGCFVL   EGPKLVASTQ   AALA*
  EDQLKTVMGD   FAQFVDKCCK   AADKDNCFAT   EGPNLVARSK   EALA*
  KNHIDEWLLE   FLKMVQKCCT   ADEHQPCFDT   EKPVLIEHCQ   KLHP*
  EDHLKTISTK   YHTMKEKCCA   AEDQAACFTE   EAPKLVSESA   ELVKV
```

FIG. 2-3

BIOLOGICALLY ACTIVE PROTEIN FRAGMENTS CONTAINING SPECIFIC BINDING REGIONS OF SERUM ALBUMIN OR RELATED PROTEINS

This application is a continuation of application Ser. No. 08/024,547, filed Mar. 1, 1993, now abandoned.

FIELD OF THE INVENTION

The invention relates to the specific binding regions of serum albumin and related proteins and to biologically active protein fragments containing these specific binding regions that can be safely and economically produced using conventional recombinant DNA techniques.

BACKGROUND OF THE INVENTION

The serum albumins belong to a multigene family of proteins that includes alpha-fetoprotein (AFP) and human group-specific component (Gc) or vitamin D-binding protein. The members of this multigene family are typically comprised of relatively large multi-domain proteins, and the serum albumins are major soluble protein constituents of the circulatory system which have many physiological functions. The albumins and their related proteins contribute significantly to colloid osmotic blood pressure and aid in the transport, distribution and metabolism of many endogenous and exogenous ligands. These ligands represent a spectrum of chemically diverse molecules, including fatty acids, amino acids (notably tryptophan and cysteine), steroids, metals such as calcium, copper and zinc, and numerous pharmaceuticals. They are thought to facilitate transfer of many ligands across organ-circulatory interfaces such as the liver, intestine, kidney and brain, and evidence suggests the existence of an albumin cell surface receptor (see Schnitzer et al., PNAS 85:6773 (1988)).

In addition, serum albumins are also found in tissues and secreted fluids throughout the body. For example, it is estimated that albumin in evascular protein comprises 60% of the body's total albumin. In humans, human serum albumin, or HSA, is a protein of about 65,000 daltons in molecular weight and contains 585 amino acids. Its amino acid sequence contains a total of 17 disulphide bridges, one free thiol (Cys 34), and a single tryptophan (Trp 214). The disulphides are positioned in a repeating series of nine loop-link-loop structures centered around eight sequential Cys—Cys pairs.

Studies of serum albumins have been made on a variety of animal species, and it has been determined that approximately 61% of the amino acid sequences are conserved among the known sequences of bovine, rat and human serum albumins. More recently, additional sequences for the albumins have been determined with regard to a wide ranging group of vertebrates including sheep, frog, salmon, mouse, pig and even sea lampreys. Most of these proteins share high sequence homology and all of them share the characteristic repeating series of disulphide bridges. All members of the albumin multigene family for which sequences have been determined have internal sequence homology (from two- to seven-fold), suggesting that the proteins evolved from a common ancestral protein of possibly about 190 amino acids. Other studies have confirmed this homology (see, e.g., Carter et al., Science 244:1195 (1989)).

Currently, there are literally thousands of applications for serum albumin protein and its related proteins, Gc and AFP, and most often these applications have used the native serum albumin family of proteins obtained from bovine or human sources. Unfortunately, at present, the numerous concerns with regard to the safety of albumin-containing plasma isolated from natural sources have greatly restricted the availability of albumin proteins for many of these applications. Included among these concerns is the heightened possibility that the plasma from which the albumins are obtained will be infected with various viral contaminants including HIV or other AIDS-related viruses, Hepatitis-B, herpes, and a number of other potentially pathogenic microorganisms.

Because of these concerns, there have been many attempts to prepare recombinant DNA sequences coding for serum albumins which can be used in the artificial production of this important molecule. However, unfortunately, these attempts have also been generally unsuccessful because of the fact that like most large proteins, serum albumins denature quite readily and are practically impossible to produce in usable quantities by genetic engineering. It thus has remained a problem to develop artificial serum solutions which are stable and which can maintain the biologically activity of natural serum albumins.

Clearly, the utility of the serum albumin molecules is based in large part in their ability to bind and thus transport a wide variety of important macromolecules so as to regulate a number of physiological functions in humans and animals. However, although the binding properties of serum albumin have been well-established, the precise nature and location of those binding regions have not. Thus, although certain amino acid sites, such as Lys 199 and Tyr 411 have been identified as involved in acetylation (see Hagag et al., Biochemistry 22:2420 (1983)) and esterification (see Sollene et al., Molec. Pharmac. 14:754 (1979)), very little has been previously been known about the binding sites of the serum albumins.

There has thus been a long-felt and unfulfilled need in the art to identify specific binding sites in the serum albumin family of proteins so as to allow the large-scale production of protein fragments having the same binding properties and biological activity as whole serum albumins. Since such smaller genetically engineered polypeptides are much more easily expressed and produced in large quantities than the full albumins, the identification of these specific binding sites would make commercial isolation and production of artificial polypeptides having all of the same binding properties of natural albumins much more economically and technically feasible.

SUMMARY OF THE INVENTION

In accordance with the present invention, it has now been discovered that specific portions of the serum albumin multigene family of proteins, specifically those portions known as subdomains IIA and IIIA, are primarily responsible for the binding properties of serum albumin and its related proteins, and that biologically active artificial serums prepared from protein fragments containing at least one of these binding regions can be produced much more easily than serums containing the whole protein. In particular, the sequence for binding subdomain IIA appears to be from about amino acids 190 through 300 on the albumin molecules, and subdomain IIIA appears to be located on the polypeptide at roughly from amino acid 380 to about amino acid 495.

Further, it also appears that a fusion product, which includes not only the above binding subdomains IIA and IIIA but an additional region IIB, is also useful in binding, and this fusion product is coded on the polypeptide at about amino acid 190 through 495. The discovery that the binding of the albumin family of proteins is based primarily on these specific binding regions will thus allow for the production of protein fragments containing one or more of these binding regions which are capable of exhibiting the same biological activity as the whole albumin protein.

It is thus an object of the present invention to provide protein fragments containing at least one of the binding sites from the serum albumin family of proteins so as to allow the production of biologically active serum which does not contain albumin family proteins obtained from natural sources.

It is further an object of the present invention to provide novel artificial polypeptides which can be constructed using conventional recombinant DNA techniques and which can be more safely, economically and effectively used in a variety of applications which call for serum albumins or other related proteins.

It is even further an object of the present invention to construct biologically active protein fragments that are useful for a wide variety of physiological, chromatographic and crystallographic functions which can be produced in large quantities and which can effectively be used instead of whole serum albumins obtained from natural or artificial sources.

These and objects of the present invention are set forth in, or will become obvious from, the description of the preferred embodiments provided hereinbelow.

BRIEF DESCRIPTION OF THE DRAWING FIGURES:

FIG. 2 is a representation of the sequence homology of the amino acid sequences of a variety of the serum albumins including from top to bottom, human serum albumin (SEQ ID NO:3), bovine serum albumin (SEQ ID NO:4), equine serum albumin (SEQ ID NO:5), ovine serum albumin (SEQ ID NO:6), rat serum albumin (SEQ ID NO:7), frog serum albumin (SEQ ID NO:8), and salmon serum albumin (SEQ ID NO:9).

Figure 1:
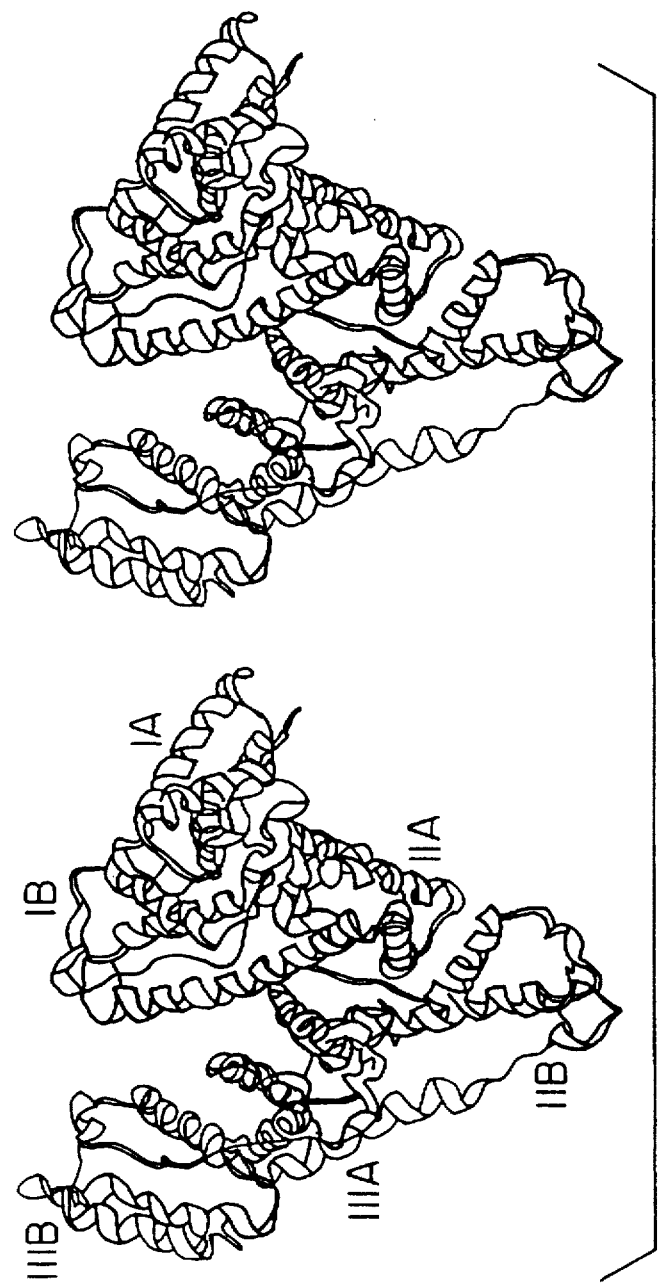
FIG. 1 is a stereo view illustrating the overall topology of human serum albumin.

DETAILED DESCRIPTION OF THE PREFERRED EMBODIMENTS:

In accordance with the present invention, the characteristic binding locations of the serum albumin family of proteins were determined crystallographically at 3.1 Angstroms using a wild-type human serum albumin (HSA) and at 2.8 Angstroms for a recombinant form of HSA expressed in yeast (rHSA). A complete description of the structural determination of a serum albumin protein through crystallographic means is set forth in Nature, Vol. 358:209 (July 1992), incorporated herein by reference. These crystallographic studies confirmed that the topology of serum albumins such as human serum albumin is created by a repeating series of six helical subdomains, known as IA, IB, IIA, IIB, IIIA and IIIB. These six subdomains assemble to form a heart-shaped molecule, as had previously been determined in the stereo view illustration as observed in FIG. 1. However, the previous determinations of the serum albumin structure gave little insight into its binding locations, and it was previously thought that a number of the helical subdomains were involved in albumin binding.

The detailed crystallography studies indicated that contrary to the prior albumin models, the principal binding regions were located specifically in subdomain IIA and subdomain IIIA. The binding cavity in region IIIA appears to be the most active and accommodating on the human serum albumin, and many ligands have been found to preferentially bind in this region, such as digitoxin, ibuprofen and tryptophan. Other ligand binding affinities have been tested, and relative binding locations have now been determined crystallographically for several ligands at low resolution, as set forth below in Table 1. These tests showed that aspirin and iodinated aspirin analogues show nearly equal distributions between binding sites IIA and IIIA, while the composition known as Warfarin appears to occupy a single site in IIA. Further, the amino acid residues that have previously been thought to be involved in the binding process, Trp 214, Lys 199 and Tyr 411, are all located strategically in the IIA or IIIA regions.

TABLE I

Ligand binding locations to HSA

| Ligand | D | N | $R_f$ | Observed location |
|---|---|---|---|---|
| Aspirin | 4.0 | 7362 | 0.11 | IIA IIIA |
| Warfarin | 5.0 | 2555 | 0.167 | IIA |
| Diazepam | 6.8 | 2075 | 0.118 | IIIA |
| Digitoxin | 5.0 | 3751 | 0.137 | IIIA |
| Clofibrate | 6.0 | 2175 | 0.138 | IIIA |
| Ibuprofen | 6.0 | 2402 | 0.215 | IIIA |
| AZT | 4.0 | 7548 | 0.124 | IIIA |
| IS | 4.0 | 6334 | 0.19 | IIA IIIA |
| DIS | 4.0 | 4734 | 0.20 | IIA IIIA |
| TIB | 4.0 | 5431 | 0.12 | IIA IIIA |

Ligand-HSA complexes and X-ray diffraction data were obtained in a manner as previously described in Table 1. The observed locations refer to the primary binding sites.
D, Resolution or d-spacing in Å.
N, Number of paired unique reflections with F > 5σ.
$R_f$, $\Sigma F_{PH} - F_P / \Sigma F_P$.
AZT, 3'-Azido-3'-deoxythymidine.
IS, 5-iodosalicylic acid.
DIS, 3,5-Diiodosalicylic acid.
TIB, 2,3,5-Triiodobenzoic acid.

The structural determination of the binding regions of the serum albumin family of proteins shows that the amino acid sequences appear to be homologous along the various serum albumins, which is evidenced in FIG. 2 wherein the amino acid sequences of human, bovine, equine, ovine, rat, frog and salmon albumins are compared. The crystallographic studies conducted in order to locate and identify the albumin protein binding sites appear to show that the IIA subdomain is one of the key binding sites of the albumin protein, and this region corresponds to an amino acid sequence beginning at approximately amino acid number 190 of the albumin protein and extending to about amino acid number 300. In one specific embodiment, the sequence for the binding region IIA as determined in bovine serum albumin is set forth at in SEQ ID NO:1, and this sequence runs from amino acid number 190 through amino acid number 298 on bovine serum albumin.

The crystallographic studies carried out by the inventor also revealed that the IIIA subdomain was another key binding site on the albumin family of proteins, and this binding subdomain corresponds to a sequence of amino acids which starts at about amino acid number 375 and extends to about amino acid number 495. In another specific embodiment, binding region IIIA has an amino acid sequence as set forth in SEQ ID NO:2, and this sequence appears to run from amino acid 378 through 494. In accordance with the present invention, a protein fragment containing at least one of the binding regions IIA or IIIA discussed above can be prepared which will have the same or similar biological activity as a whole natural serum albumin.

In addition to the specific binding regions IIA or IIIA discussed above, there also appears to be an additional fusion product of subdomains IIA and IIIA that also acts to give serum albumin some of its binding properties. This fusion product appears to be a fragment that includes not only binding regions IIA and IIIA, but subdomain IIB as well. A protein fragment in accordance with the present invention can thus also be constructed which contains the region including IIA, IIB and IIIA, and this region corresponds roughly to an amino acid sequence extending from about amino acid 190 to about amino acid 495 on a serum albumin family protein. Further, it is possible that such a fragment would be even more biologically active and more likely to preserve all of the original binding peculiarities associated with the albumin family of proteins since there are sometimes measurable allosteric effects between the subdomains.

The isolation of any of the specific albumin family binding regions discussed above is advantageous in that not only can biologically active serums be produced from isolates of these binding fragments from the natural albumins, but recombinant methods can be used as well to construct protein fragments containing only these specific binding regions. In fact, the present invention is particularly advantageous because the protein fragments of the invention can be prepared artificially using conventional recombinant DNA techniques, and these fragments will be safer, more stable and more effective than the natural serums in a variety of applications, including column chromatography, biosensors, crystallographic or solution drug binding experimentation, and a wide range of medical and biochemical procedures and experimentation. Thus, although isolates of the albumin proteins can be produced according to the present invention with one or more of the actual binding regions obtained from natural sources, it is preferred that conventional recombinant techniques be used to manufacture the protein fragments containing or corresponding to at least one of the binding regions discussed above, and these artificial fragments can be recovered and/or purified so as to useful in all applications where natural serum albumin would be used.

In another aspect of the present invention, it has also been discovered that key invariant residues that are involved in the ligand binding subdomains and which are conserved in most or all the known albumins, and these key residues would thus appear to be primarily responsible for the binding properties attributed to these regions. Based on an examination of the sequence homology as observed in FIG. 2, and based on other studies involving the crystallographic patterns of the albumin proteins, it appears that there are certain key residues that are conserved between all of the determined albumin sequences and that fit precisely in the binding regions IIA and IIIA discussed above. In particular, these key invariant or conserved residues appear to be at amino acid residues 257 and 260 of the IIA region, and at amino acid residues 390, 391, 410, 411, 423, 437, 450, 453 and 485 of the IIIA region. It is thus contemplated that any protein fragment that is constructed to contain at least the key residues of either or both of the subdomains IIA and IIIA as set forth above will also exhibit binding properties equivalent or similar to that of the whole albumin molecules.

In summary, the present invention allows for the production of protein fragments containing specific binding sites of the albumin proteins which can be generated by conventional recombinant DNA techniques and which have the same or similar binding properties as the natural serum albumins. It is thus contemplated that these protein fragments can be prepared efficiently and economically in large quantities so as to substituted for the natural form of the albumins in a variety of applications without any loss of binding strength. As set forth herein, the term "protein fragment" is well understood the those skilled in the art and generally refers to those polypeptides comprising an amino acid sequence that only constitutes a portion of a whole protein molecule.

These protein fragments, when constructed artificially using state-of-the-art recombinant means, will not only have the same or similar biological activity of the natural whole albumin proteins, but will also be safer that the natural form of the albumins since they will not carry many of the other viral or other pathogenic contaminants that are found in the natural products. As set forth herein, the term "biological activity" is well understood to one skilled in the art and is used generally to refer to the ability of a particular molecule, such as a whole protein or a particularly active fragment from a whole protein, to successfully carry out any of a number of biological or biochemical functions.

When preparing fragments containing the specific binding regions of the present invention, it will be well understood by those skilled in the art that a number of alternate sequences can be prepared which will differ in some slight manner from the binding regions as discussed above, yet which are considered within the scope of the invention. For example, these alternate embodiments include those fragments or sequences which have slight variations as to specific amino acids, such as those which include an addition or deletion of a particular amino acid, possibly at the leading or trailing end of the fragment, which maintain the binding properties of the albumin family of proteins in the manner set forth above. Additionally, those sequences which contain certain changes in specific amino acids which may enhance or decrease the binding affinity of various compounds, or reduce the likelihood of producing an antigenic response, will also be within the scope of the invention as would be obvious to one of ordinary skill in the art. Finally, as set forth above, it is contemplated that because the subdomain regions of the multigene family of albumin proteins appear to be the same or similar, the biologically active protein fragments of the present invention can be constructed from specific binding regions of any of the proteins of the serum albumin family, such as the Gc and AFP proteins discussed above. All of these embodiments are deemed to be covered within the scope of the present invention which is set forth in the claims appended hereto.

What is claimed is:

1. A serum albumin protein fragment consisting of at least one serum albumin binding region selected from the group consisting of binding region subdomain IIA and binding region subdomain IIIA.

2. A serum albumin protein fragment according to claim 1 wherein the serum albumin binding region consists of binding region subdomain IIA.

3. A serum albumin protein fragment according to claim 1 wherein the serum albumin binding region consists of binding region subdomain IIIA.

4. A serum albumin protein fragment according to claim 1 wherein the serum albumin binding region consists of binding region subdomains IIA, IIB and IIIA.

5. A serum albumin protein fragment according to claim 1 wherein the serum albumin binding region is a binding region of a serum albumin selected from the group consisting of human, bovine, equine, ovine, rat, frog, sheep, salmon, mouse, and sea lamprey serum albumin proteins.

6. A serum albumin protein fragment according to claim 5 wherein the serum albumin binding region is a human serum albumin binding region.

7. A serum albumin protein fragment according to claim 5 wherein the serum albumin binding region is an equine serum albumin binding region.

8. A serum albumin protein fragment according to claim 5 wherein the serum albumin binding region is a bovine serum albumin binding region.

9. A serum albumin protein fragment according to claim 8 wherein the serum albumin binding region consists of SEQ ID NO: 1.

10. A serum albumin protein fragment according to claim 8, wherein the serum albumin binding region consists of SEQ ID NO:2.

11. A serum albumin protein fragment according to claim 4 wherein the serum albumin binding region consists of amino acids 190 to 494 of SEQ ID NO:4.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 109 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:1:

```
Ala Ser Ser Ala Arg Gln Arg Leu Arg Cys Ala Ser Ile Gln Lys Phe
1               5                   10                  15

Gly Glu Arg Ala Leu Lys Ala Trp Ser Val Ala Arg Leu Ser Gln Lys
                20                  25                  30

Phe Pro Lys Ala Glu Phe Val Glu Val Thr Lys Leu Val Thr Asp Leu
            35                  40                  45

Thr Lys Val His Lys Glu Cys Cys His Gly Asp Leu Leu Glu Cys Ala
        50                  55                  60

Asp Asp Arg Ala Asp Leu Ala Lys Tyr Ile Cys Asp Asn Gln Asp Thr
65                  70                  75                  80

Ile Ser Ser Lys Leu Lys Glu Cys Cys Asp Lys Pro Leu Leu Glu Lys
                85                  90                  95

Ser His Cys Ile Ala Glu Val Glu Lys Asp Ala Ile Pro
                100                 105
```

( 2 ) INFORMATION FOR SEQ ID NO:2:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
His Leu Val Asp Glu Pro Gln Asn Leu Ile Lys Gln Asn Cys Asp Gln
1               5                   10                  15

Phe Glu Lys Leu Gly Glu Tyr Gly Phe Gln Asn Ala Leu Ile Val Arg
                20                  25                  30

Tyr Thr Arg Lys Val Pro Gln Val Ser Thr Pro Thr Leu Val Glu Val
            35                  40                  45

Ser Arg Ser Leu Gly Lys Val Gly Thr Arg Cys Cys Thr Lys Pro Glu
        50                  55                  60

Ser Glu Arg Met Pro Cys Thr Glu Asp Tyr Leu Ser Leu Ile Leu Asn
65                  70                  75                  80

Arg Leu Cys Val Leu His Glu Lys Thr Pro Val Ser Glu Lys Val Thr
                85                  90                  95

Lys Cys Cys Thr Glu Ser Leu Val Asn Arg Arg Pro Cys Phe Ser Ala
```

Leu Thr Pro Asp Glu
            115

(2) INFORMATION FOR SEQ ID NO:3:

(i) SEQUENCE CHARACTERISTICS:
       (A) LENGTH: 585 amino acids
       (B) TYPE: amino acid
       (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:3:

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

|     |     |     |     |     |     |     |     |     |     |     |     |     |     |     |
|---|---|---|---|---|---|---|---|---|---|---|---|---|---|---|
| Leu 305 | Ala | Ala | Asp | Phe 310 | Val | Glu | Ser | Lys | Asp 315 | Val | Cys | Lys | Asn | Tyr Ala 320 |
| Glu | Ala | Lys | Asp | Val 325 | Phe | Leu | Gly | Met | Phe 330 | Leu | Tyr | Glu | Tyr | Ala Arg 335 |
| Arg | His | Pro | Asp 340 | Tyr | Ser | Val | Val | Leu 345 | Leu | Leu | Arg | Leu | Ala 350 | Lys Thr |
| Tyr | Glu | Thr 355 | Thr | Leu | Glu | Lys | Cys 360 | Cys | Ala | Ala | His | Asp 365 | Pro | His Glu |
| Cys | Tyr 370 | Ala | Lys | Val | Phe | Asp 375 | Glu | Phe | Lys | Pro | Leu 380 | Val | Glu | Glu Pro |
| Gln 385 | Asn | Leu | Ile | Lys | Gln 390 | Asn | Cys | Glu | Leu | Phe 395 | Lys | Gln | Leu | Gly Glu 400 |
| Tyr | Lys | Phe | Gln | Asn 405 | Ala | Leu | Leu | Val | Arg 410 | Tyr | Thr | Lys | Lys 415 | Val Pro |
| Gln | Val | Ser | Thr 420 | Pro | Thr | Leu | Val | Glu 425 | Val | Ser | Arg | Asn | Leu 430 | Gly Lys |
| Val | Gly | Ser 435 | Lys | Cys | Cys | Lys | His 440 | Pro | Glu | Ala | Lys | Arg 445 | Met | Pro Cys |
| Ala | Glu | Asp 450 | Tyr | Leu | Ser | Val 455 | Val | Leu | Asn | Gln | Leu 460 | Cys | Val | Leu His |
| Glu 465 | Lys | Thr | Pro | Val | Ser 470 | Asp | Arg | Val | Thr | Lys 475 | Cys | Cys | Thr | Glu Ser 480 |
| Leu | Val | Asn | Arg | Arg 485 | Pro | Cys | Phe | Ser | Ala 490 | Leu | Glu | Val | Asp | Glu Thr 495 |
| Tyr | Val | Pro | Lys 500 | Glu | Phe | Asn | Ala | Glu 505 | Thr | Phe | Thr | Phe | His 510 | Ala Asp |
| Ile | Cys | Thr 515 | Leu | Ser | Glu | Lys | Glu 520 | Arg | Gln | Ile | Lys | Lys 525 | Gln | Thr Ala |
| Leu | Val | Glu 530 | Leu | Val | Lys | His 535 | Lys | Pro | Lys | Ala | Thr 540 | Lys | Glu | Gln Leu |
| Lys 545 | Ala | Val | Met | Asp | Asp 550 | Phe | Ala | Ala | Phe | Val 555 | Glu | Lys | Cys | Cys Lys 560 |
| Ala | Asp | Asp | Lys | Glu 565 | Thr | Cys | Phe | Ala | Glu 570 | Glu | Gly | Lys | Lys | Leu Val 575 |
| Ala | Ala | Ser | Gln 580 | Ala | Ala | Leu | Gly | Leu 585 |     |     |     |     |     |     |

(2) INFORMATION FOR SEQ ID NO:4:

(i) SEQUENCE CHARACTERISTICS:
(A) LENGTH: 583 amino acids
(B) TYPE: amino acid
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:4:

|     |     |     |     |     |     |     |     |     |     |     |     |     |     |     |
|---|---|---|---|---|---|---|---|---|---|---|---|---|---|---|
| Asp 1 | Thr | His | Lys | Ser 5 | Glu | Ile | Ala | His | Arg 10 | Phe | Lys | Asp | Leu | Gly Glu 15 |
| Glu | His | Phe | Lys 20 | Gly | Leu | Val | Leu | Ile 25 | Ala | Phe | Ser | Gln | Tyr 30 | Leu Gln |
| Gln | Cys | Pro 35 | Phe | Asp | Glu | His | Val 40 | Lys | Leu | Val | Asn | Glu 45 | Leu | Thr Glu |

| | | | | | | | | | | | | | |
|---|---|---|---|---|---|---|---|---|---|---|---|---|---|
|Phe|Ala|Lys|Thr|Cys|Val|Ala|Asp|Glu|Ser|His|Ala|Gly|Cys|Glu|Lys|
| |50| | | |55| | | | |60| | | | | |
|Ser|Leu|His|Thr|Leu|Phe|Gly|Asp|Glu|Leu|Cys|Lys|Val|Ala|Ser|Leu|
|65| | | | |70| | | |75| | | | | |80|
|Arg|Glu|Thr|Tyr|Gly|Asp|Met|Ala|Asp|Cys|Cys|Glu|Lys|Gln|Glu|Pro|
| | | | |85| | | | |90| | | | |95| |
|Glu|Arg|Asn|Glu|Cys|Phe|Leu|Ser|His|Lys|Asp|Asp|Ser|Pro|Asp|Leu|
| | | |100| | | | |105| | | | |110| | |
|Pro|Lys|Leu|Lys|Pro|Asp|Pro|Asn|Thr|Leu|Cys|Asp|Glu|Phe|Lys|Ala|
| | | |115| | | | |120| | | | |125| | |
|Asp|Glu|Lys|Lys|Phe|Trp|Gly|Lys|Tyr|Leu|Tyr|Glu|Ile|Ala|Arg|Arg|
| | |130| | | | |135| | | | |140| | | |
|His|Pro|Tyr|Phe|Tyr|Ala|Pro|Glu|Leu|Leu|Tyr|Tyr|Ala|Asn|Lys|Tyr|
|145| | | | | |150| | | | |155| | | |160|
|Asn|Gly|Val|Phe|Gln|Glu|Cys|Cys|Gln|Ala|Glu|Asp|Lys|Gly|Ala|Cys|
| | | | |165| | | | |170| | | | |175| |
|Leu|Leu|Pro|Lys|Ile|Glu|Thr|Met|Arg|Glu|Lys|Val|Leu|Ala|Ser|Ser|
| | | |180| | | | |185| | | | |190| | |
|Ala|Arg|Gln|Arg|Leu|Arg|Cys|Ala|Ser|Ile|Gln|Lys|Phe|Gly|Glu|Arg|
| | |195| | | | |200| | | | |205| | | |
|Ala|Leu|Lys|Ala|Trp|Ser|Val|Ala|Arg|Leu|Ser|Gln|Lys|Phe|Pro|Lys|
| |210| | | | |215| | | | |220| | | | |
|Ala|Glu|Phe|Val|Glu|Val|Thr|Lys|Leu|Val|Thr|Asp|Leu|Thr|Lys|Val|
|225| | | | |230| | | | |235| | | | |240|
|His|Lys|Glu|Cys|Cys|His|Gly|Asp|Leu|Leu|Glu|Cys|Ala|Asp|Asp|Arg|
| | | | |245| | | | |250| | | | |255| |
|Ala|Asp|Leu|Ala|Lys|Tyr|Ile|Cys|Asp|Asn|Gln|Asp|Thr|Ile|Ser|Ser|
| | | |260| | | | |265| | | | |270| | |
|Lys|Leu|Lys|Glu|Cys|Cys|Asp|Lys|Pro|Leu|Leu|Glu|Lys|Ser|His|Cys|
| | |275| | | | |280| | | | |285| | | |
|Ile|Ala|Glu|Val|Glu|Lys|Asp|Ala|Ile|Pro|Glu|Asn|Leu|Pro|Pro|Leu|
| |290| | | | |295| | | | |300| | | | |
|Thr|Ala|Asp|Phe|Ala|Glu|Asp|Lys|Asp|Val|Cys|Lys|Asn|Tyr|Gln|Glu|
|305| | | | |310| | | | |315| | | | |320|
|Ala|Lys|Asp|Ala|Phe|Leu|Gly|Ser|Phe|Leu|Tyr|Glu|Tyr|Ser|Arg|Arg|
| | | | |325| | | | |330| | | | |335| |
|His|Pro|Glu|Tyr|Ala|Val|Ser|Val|Leu|Leu|Arg|Leu|Ala|Lys|Glu|Tyr|
| | | |340| | | | |345| | | | |350| | |
|Glu|Ala|Thr|Leu|Glu|Glu|Cys|Cys|Ala|Lys|Asp|Asp|Pro|His|Ala|Cys|
| | |355| | | | |360| | | | |365| | | |
|Tyr|Ser|Thr|Val|Phe|Asp|Lys|Leu|Lys|His|Leu|Val|Asp|Glu|Pro|Gln|
| |370| | | | |375| | | | |380| | | | |
|Asn|Leu|Ile|Lys|Gln|Asn|Cys|Asp|Gln|Phe|Glu|Lys|Leu|Gly|Glu|Tyr|
|385| | | | |390| | | | |395| | | | |400|
|Gly|Phe|Gln|Asn|Ala|Leu|Ile|Val|Arg|Tyr|Thr|Arg|Lys|Val|Pro|Gln|
| | | | |405| | | | |410| | | | |415| |
|Val|Ser|Thr|Pro|Thr|Leu|Val|Glu|Val|Ser|Arg|Ser|Leu|Gly|Lys|Val|
| | | |420| | | | |425| | | | |430| | |
|Gly|Thr|Arg|Cys|Cys|Thr|Lys|Pro|Glu|Ser|Glu|Arg|Met|Pro|Cys|Thr|
| | |435| | | | |440| | | | |445| | | |
|Glu|Asp|Tyr|Leu|Ser|Leu|Ile|Leu|Asn|Arg|Leu|Cys|Val|Leu|His|Glu|
| |450| | | | |455| | | | |460| | | | |
|Lys|Thr|Pro|Val|Ser|Glu|Lys|Val|Thr|Lys|Cys|Cys|Thr|Glu|Ser|Leu|

|       |       |       |       | 465 |       |       |       |     | 470 |       |       |       |       | 475 |       |       |       | 480 |
|-------|-------|-------|-------|-----|-------|-------|-------|-----|-----|-------|-------|-------|-------|-----|-------|-------|-------|-----|

Val  Asn  Arg  Arg  Pro  Cys  Phe  Ser  Ala  Leu  Thr  Pro  Asp  Glu  Thr  Tyr
                    485                      490                495

Val  Pro  Lys  Ala  Phe  Asp  Glu  Lys  Leu  Phe  Thr  Phe  His  Ala  Asp  Ile
                    500                      505                510

Cys  Thr  Leu  Pro  Asp  Thr  Glu  Lys  Gln  Ile  Lys  Lys  Gln  Thr  Ala  Leu
               515                      520                525

Val  Glu  Leu  Leu  Lys  His  Lys  Pro  Lys  Ala  Thr  Glu  Glu  Gln  Leu  Lys
          530                      535                540

Thr  Val  Met  Glu  Asn  Phe  Val  Ala  Phe  Val  Asp  Lys  Cys  Cys  Ala  Ala
545                      550                      555                560

Asp  Asp  Lys  Glu  Ala  Cys  Phe  Ala  Val  Glu  Gly  Pro  Lys  Leu  Val  Val
                    565                      570                575

Ser  Thr  Gln  Thr  Ala  Leu  Ala
                    580

(2) INFORMATION FOR SEQ ID NO:5:

(i) SEQUENCE CHARACTERISTICS:
        (A) LENGTH: 583 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:5:

Asp  Thr  His  Lys  Ser  Glu  Ile  Ala  His  Arg  Phe  Asn  Asp  Leu  Gly  Glu
1               5                        10                      15

Lys  His  Phe  Lys  Gly  Leu  Val  Leu  Val  Ala  Phe  Ser  Gln  Tyr  Leu  Gln
               20                       25                      30

Gln  Cys  Pro  Phe  Glu  Asp  His  Val  Lys  Leu  Val  Asn  Glu  Val  Thr  Glu
               35                       40                      45

Phe  Ala  Lys  Lys  Cys  Ala  Ala  Asp  Glu  Ser  Ala  Glu  Asn  Cys  Asp  Lys
     50                       55                       60

Ser  Leu  His  Thr  Leu  Phe  Gly  Asp  Lys  Leu  Cys  Thr  Val  Ala  Thr  Leu
65                       70                       75                      80

Arg  Ala  Thr  Tyr  Gly  Glu  Leu  Ala  Asp  Cys  Cys  Glu  Lys  Gln  Glu  Pro
               85                       90                      95

Glu  Arg  Asn  Glu  Cys  Phe  Leu  Thr  His  Lys  Asp  Asp  His  Pro  Asn  Leu
               100                      105                     110

Pro  Lys  Leu  Lys  Pro  Glu  Pro  Asp  Ala  Gln  Cys  Ala  Ala  Phe  Gln  Glu
               115                      120                     125

Asp  Pro  Asp  Lys  Phe  Leu  Gly  Lys  Tyr  Leu  Tyr  Glu  Val  Ala  Arg  Arg
               130                      135                     140

His  Pro  Tyr  Phe  Tyr  Gly  Pro  Glu  Leu  Leu  Phe  His  Ala  Glu  Glu  Tyr
145                      150                      155                     160

Lys  Ala  Asp  Phe  Thr  Glu  Cys  Cys  Pro  Ala  Asp  Asp  Lys  Leu  Ala  Cys
                    165                      170                     175

Leu  Ile  Pro  Lys  Leu  Asp  Ala  Leu  Lys  Glu  Arg  Ile  Leu  Leu  Ser  Ser
               180                      185                     190

Ala  Lys  Glu  Arg  Leu  Lys  Cys  Ser  Ser  Phe  Gln  Asn  Phe  Gly  Glu  Arg
          195                      200                      205

-continued

| | | | | | | | | | | | | | | |
|---|---|---|---|---|---|---|---|---|---|---|---|---|---|---|
| Ala | Val | Lys | Ala | Trp | Ser | Val | Ala | Arg | Leu | Ser | Gln | Lys | Phe | Pro | Lys |
| | 210 | | | | 215 | | | | | 220 | | | | |
| Ala | Asp | Phe | Ala | Glu | Val | Ser | Lys | Ile | Val | Thr | Asp | Leu | Thr | Lys | Val |
| 225 | | | | | 230 | | | | | 235 | | | | | 240 |
| His | Lys | Glu | Cys | Cys | His | Gly | Asp | Leu | Leu | Glu | Cys | Ala | Asp | Asp | Arg |
| | | | | 245 | | | | | 250 | | | | | 255 | |
| Ala | Asp | Leu | Ala | Lys | Tyr | Ile | Cys | Glu | His | Gln | Asp | Ser | Ile | Ser | Gly |
| | | | 260 | | | | | 265 | | | | | 270 | | |
| Lys | Leu | Lys | Ala | Cys | Cys | Asp | Lys | Pro | Leu | Leu | Gln | Lys | Ser | His | Cys |
| | | 275 | | | | 280 | | | | | 285 | | | | |
| Ile | Ala | Glu | Val | Lys | Glu | Asp | Leu | Pro | Ser | Asp | Ile | Pro | Ala | Leu |
| | 290 | | | | | 295 | | | | | 300 | | | | |
| Ala | Ala | Asp | Phe | Ala | Glu | Asp | Lys | Glu | Ile | Cys | Lys | His | Tyr | Lys | Asp |
| 305 | | | | | 310 | | | | | 315 | | | | | 320 |
| Ala | Lys | Asp | Val | Phe | Leu | Gly | Thr | Phe | Leu | Tyr | Glu | Tyr | Ser | Arg | Arg |
| | | | | 325 | | | | | 330 | | | | | 335 | |
| His | Pro | Asp | Tyr | Ser | Val | Ser | Leu | Leu | Leu | Arg | Ile | Ala | Lys | Thr | Tyr |
| | | | 340 | | | | | 345 | | | | | 350 | | |
| Glu | Ala | Thr | Leu | Glu | Lys | Cys | Cys | Ala | Glu | Ala | Asp | Pro | Pro | Ala | Cys |
| | | 355 | | | | | 360 | | | | | 365 | | | |
| Tyr | Arg | Thr | Val | Phe | Asp | Gln | Phe | Thr | Pro | Leu | Val | Glu | Glu | Pro | Lys |
| | 370 | | | | | 375 | | | | | 380 | | | | |
| Ser | Leu | Val | Lys | Lys | Asn | Cys | Asp | Leu | Phe | Glu | Glu | Val | Gly | Glu | Tyr |
| 385 | | | | | 390 | | | | | 395 | | | | | 400 |
| Asp | Phe | Gln | Asn | Ala | Leu | Ile | Val | Arg | Tyr | Thr | Lys | Lys | Ala | Pro | Gln |
| | | | | 405 | | | | | 410 | | | | | 415 | |
| Val | Ser | Thr | Pro | Thr | Leu | Val | Glu | Ile | Gly | Arg | Thr | Leu | Gly | Lys | Val |
| | | | 420 | | | | | 425 | | | | | 430 | | |
| Gly | Ser | Arg | Cys | Cys | Lys | Leu | Pro | Glu | Ser | Glu | Arg | Leu | Pro | Cys | Ser |
| | | | 435 | | | | | 440 | | | | | 445 | | |
| Glu | Asn | His | Leu | Ala | Leu | Ala | Leu | Asn | Arg | Leu | Cys | Val | Leu | His | Glu |
| | | | | 450 | | | | 455 | | | | | 460 | | |
| Lys | Thr | Pro | Val | Ser | Glu | Lys | Ile | Thr | Lys | Cys | Cys | Thr | Asp | Ser | Leu |
| 465 | | | | | 470 | | | | | 475 | | | | | 480 |
| Ala | Glu | Arg | Arg | Pro | Cys | Phe | Ser | Ala | Leu | Glu | Leu | Asp | Glu | Gly | Tyr |
| | | | | 485 | | | | | 490 | | | | | 495 | |
| Pro | Val | Lys | Glu | Phe | Lys | Ala | Glu | Thr | Phe | Thr | Phe | His | Ala | Asp | Ile |
| | | | 500 | | | | | 505 | | | | | 510 | | |
| Cys | Thr | Leu | Pro | Glu | Asp | Glu | Lys | Gln | Ile | Lys | Lys | Gln | Ser | Ala | Leu |
| | | 515 | | | | | 520 | | | | | 525 | | | |
| Ala | Glu | Leu | Val | Lys | His | Lys | Pro | Lys | Ala | Thr | Lys | Glu | Gln | Leu | Lys |
| | 530 | | | | | 535 | | | | | 540 | | | | |
| Thr | Val | Leu | Gly | Asn | Phe | Ser | Ala | Phe | Val | Ala | Lys | Cys | Cys | Gly | Arg |
| 545 | | | | | 550 | | | | | 555 | | | | | 560 |
| Glu | Asp | Lys | Glu | Ala | Cys | Phe | Ala | Glu | Glu | Gly | Pro | Lys | Leu | Val | Ala |
| | | | | 565 | | | | | 570 | | | | | 575 | |
| Ser | Ser | Gln | Leu | Ala | Leu | Ala | | | | | | | | | |
| | | | 580 | | | | | | | | | | | | |

( 2 ) INFORMATION FOR SEQ ID NO:6:

( i ) SEQUENCE CHARACTERISTICS:
        ( A ) LENGTH: 583 amino acids
        ( B ) TYPE: amino acid
        ( D ) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:6:

```
Asp Thr His Lys Ser Glu Ile Ala His Arg Phe Asn Asp Leu Gly Glu
  1               5                  10                  15
Glu Asn Phe Gln Gly Leu Val Leu Ile Ala Phe Ser Gln Tyr Leu Gln
                 20                  25                  30
Gln Cys Pro Phe Asp Glu His Val Lys Leu Val Lys Glu Leu Thr Glu
                 35                  40                  45
Phe Ala Lys Thr Cys Val Ala Asp Glu Ser His Ala Gly Cys Asp Lys
             50                  55                  60
Ser Leu His Thr Leu Phe Gly Asp Glu Leu Cys Lys Val Ala Thr Leu
 65                  70                  75                  80
Arg Glu Thr Tyr Gly Asp Met Ala Asp Cys Cys Glu Lys Gln Glu Pro
                 85                  90                  95
Glu Arg Asn Glu Cys Phe Leu Asn His Lys Asp Asp Ser Pro Asp Leu
                100                 105                 110
Pro Lys Leu Lys Pro Glu Pro Asp Thr Leu Cys Ala Glu Phe Lys Ala
                115                 120                 125
Asp Glu Lys Lys Phe Trp Gly Lys Tyr Leu Tyr Glu Val Ala Arg Arg
            130                 135                 140
His Pro Tyr Phe Tyr Ala Pro Glu Leu Leu Tyr Tyr Ala Asn Lys Tyr
145                 150                 155                 160
Asn Gly Val Phe Gln Glu Cys Cys Gln Ala Glu Asp Lys Gly Ala Cys
                165                 170                 175
Leu Leu Pro Lys Ile Asp Ala Met Arg Glu Lys Val Leu Ala Ser Ser
                180                 185                 190
Ala Arg Gln Arg Leu Arg Cys Ala Ser Ile Gln Lys Phe Gly Glu Arg
                195                 200                 205
Ala Leu Lys Ala Trp Ser Val Ala Arg Leu Ser Gln Lys Phe Pro Lys
            210                 215                 220
Ala Asp Phe Thr Asp Val Thr Lys Ile Val Thr Asp Leu Thr Lys Val
225                 230                 235                 240
His Lys Glu Cys Cys His Gly Asp Leu Leu Glu Cys Ala Asp Asp Arg
                245                 250                 255
Ala Asp Leu Ala Lys Tyr Ile Cys Asp His Gln Asp Ala Leu Ser Ser
                260                 265                 270
Lys Leu Lys Glu Cys Cys Asp Lys Pro Val Leu Glu Lys Ser His Cys
            275                 280                 285
Ile Ala Glu Val Asp Lys Asp Ala Val Pro Glu Asn Leu Pro Pro Leu
            290                 295                 300
Thr Ala Asp Phe Ala Glu Asp Lys Glu Val Cys Lys Asn Tyr Gln Glu
305                 310                 315                 320
Ala Lys Asp Val Phe Leu Gly Ser Phe Leu Tyr Glu Tyr Ser Arg Arg
                325                 330                 335
His Pro Glu Tyr Ala Val Ser Val Leu Leu Arg Leu Ala Lys Glu Tyr
                340                 345                 350
Glu Ala Thr Leu Glu Asp Cys Cys Ala Lys Glu Asp Pro His Ala Cys
            355                 360                 365
Tyr Ala Thr Val Phe Asp Lys Leu Lys His Leu Val Asp Glu Pro Gln
```

|     |     |     |     |     | 370 |     |     |     |     | 375 |     |     |     |     | 380 |     |     |
|-----|-----|-----|-----|-----|-----|-----|-----|-----|-----|-----|-----|-----|-----|-----|-----|-----|-----|

Asn Leu Ile Lys Lys Asn Cys Glu Leu Phe Glu Lys His Gly Glu Tyr
385                390                395                400

Gly Phe Gln Asn Ala Leu Ile Val Arg Tyr Thr Arg Lys Ala Pro Gln
          405                410                415

Val Ser Thr Pro Thr Leu Val Glu Ile Ser Arg Ser Leu Gly Lys Val
          420                425                430

Gly Thr Lys Cys Cys Ala Lys Pro Glu Ser Glu Arg Met Pro Cys Thr
          435                440                445

Glu Asp Tyr Leu Ser Leu Ile Leu Asn Arg Leu Cys Val Leu His Glu
450                455                460

Lys Thr Pro Val Ser Glu Lys Val Thr Lys Cys Cys Thr Glu Ser Leu
465                470                475                480

Val Asn Arg Arg Pro Cys Phe Ser Asp Leu Thr Leu Asp Glu Thr Tyr
          485                490                495

Val Pro Lys Pro Phe Asp Glu Lys Phe Phe Thr Phe His Ala Asp Ile
          500                505                510

Cys Thr Leu Pro Asp Thr Glu Lys Gln Ile Lys Lys Gln Thr Ala Leu
          515                520                525

Val Glu Leu Leu Lys His Lys Pro Lys Ala Thr Asp Glu Gln Leu Lys
530                535                540

Thr Val Met Glu Asn Phe Val Ala Phe Val Asp Lys Cys Cys Ala Ala
545                550                555                560

Asp Asp Lys Glu Gly Cys Phe Val Leu Glu Gly Pro Lys Leu Val Ala
                    565                570                575

Ser Thr Gln Ala Ala Leu Ala
          580

( 2 ) INFORMATION FOR SEQ ID NO:7:

( i ) SEQUENCE CHARACTERISTICS:
        ( A ) LENGTH: 584 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

Glu Ala His Lys Ser Glu Ile Ala His Arg Phe Lys Asp Leu Gly Glu
1              5                  10                 15

Gln His Phe Lys Gly Leu Val Leu Ile Ala Phe Ser Gln Tyr Leu Gln
          20                 25                 30

Lys Cys Pro Tyr Glu Glu His Ile Lys Leu Val Gln Glu Val Thr Asp
          35                 40                 45

Phe Ala Lys Thr Cys Val Ala Asp Glu Asn Ala Glu Asn Cys Asp Lys
50                 55                 60

Ser Ile His Thr Leu Phe Gly Asp Lys Leu Cys Ala Ile Pro Lys Leu
65                 70                 75                 80

Arg Asp Asn Tyr Gly Glu Leu Ala Asp Cys Cys Ala Lys Gln Glu Pro
                    85                 90                 95

Glu Arg Asn Glu Cys Phe Leu Gln His Lys Asp Asp Asn Pro Asn Leu
                    100                105                110

-continued

| | | | | | | | | | | | | | |
|---|---|---|---|---|---|---|---|---|---|---|---|---|---|
|Pro|Pro|Phe 115|Gln|Arg|Pro|Glu 120|Ala|Glu|Ala|Met|Cys 125|Thr|Ser|Phe|Gln|
|Glu|Asn 130|Pro|Thr|Ser|Phe|Leu 135|Gly|His|Tyr|Leu|His 140|Glu|Val|Ala|Arg|
|Arg 145|His|Pro|Tyr|Phe 150|Tyr|Ala|Pro|Glu|Leu 155|Leu|Tyr|Tyr|Ala|Glu|Lys 160|
|Tyr|Asn|Glu|Val|Leu 165|Thr|Gln|Cys|Cys|Thr 170|Glu|Ser|Asp|Lys|Ala 175|Ala|
|Cys|Leu|Thr|Pro 180|Lys|Leu|Asp|Ala|Val 185|Lys|Glu|Lys|Ala|Leu 190|Val|Ala|
|Ala|Val|Arg 195|Gln|Arg|Met|Lys|Cys 200|Ser|Ser|Met|Gln|Arg 205|Phe|Gly|Glu|
|Arg|Ala|Phe 210|Lys|Ala|Trp|Ala 215|Val|Ala|Arg|Met|Ser 220|Gln|Arg|Phe|Pro|
|Asn 225|Ala|Glu|Phe|Ala|Glu 230|Ile|Thr|Lys|Leu|Ala 235|Thr|Asp|Val|Thr|Lys 240|
|Ile|Asn|Lys|Glu|Cys 245|Cys|His|Gly|Asp|Leu 250|Leu|Glu|Cys|Ala|Asp 255|Asp|
|Arg|Ala|Glu|Leu|Ala 260|Lys|Tyr|Met|Cys|Glu 265|Asn|Gln|Ala|Thr|Ile 270|Ser|
|Ser|Lys|Leu 275|Gln|Ala|Cys|Cys|Asp 280|Lys|Pro|Val|Leu|Gln 285|Lys|Ser|Gln|
|Cys|Leu|Ala 290|Glu|Thr|Glu|His|Asp 295|Asn|Ile|Pro|Ala|Asp 300|Leu|Pro|Ser|
|Ile|Ala|Ala|Asp|Phe 310|Val|Glu|Asp|Lys|Glu|Val 315|Cys|Lys|Asn|Tyr|Ala 320|
|305||||||||||||||||
|Glu|Ala|Lys|Asp|Val 325|Phe|Leu|Gly|Thr|Phe 330|Leu|Tyr|Glu|Tyr|Ser 335|Arg|
|Arg|His|Pro|Asp 340|Tyr|Ser|Val|Ser|Leu 345|Leu|Leu|Arg|Leu|Ala 350|Lys|Lys|
|Tyr|Glu|Ala|Thr 355|Leu|Glu|Lys|Cys 360|Cys|Ala|Glu|Gly|Asp 365|Pro|Pro|Ala|
|Cys|Tyr 370|Gly|Thr|Val|Leu|Ala 375|Glu|Phe|Gln|Pro|Leu 380|Val|Glu|Glu|Pro|
|Lys 385|Asn|Leu|Val|Lys|Thr 390|Asn|Cys|Glu|Leu|Tyr 395|Glu|Lys|Leu|Gly|Glu 400|
|Tyr|Gly|Phe|Gln|Asn 405|Ala|Val|Leu|Val|Arg 410|Tyr|Thr|Gln|Lys|Ala 415|Pro|
|Gln|Val|Ser|Thr 420|Pro|Thr|Leu|Val|Glu 425|Ala|Ala|Arg|Asn|Leu 430|Gly|Arg|
|Val|Gly|Thr 435|Lys|Cys|Cys|Thr|Leu 440|Pro|Glu|Ala|Gln|Arg 445|Leu|Pro|Cys|
|Val|Glu 450|Asp|Tyr|Leu|Ser|Ala 455|Ile|Leu|Asn|Arg|Leu 460|Cys|Val|Leu|His|
|Glu|Lys 465|Thr|Pro|Val|Ser 470|Glu|Lys|Val|Thr|Lys 475|Cys|Cys|Ser|Gly|Ser 480|
|Leu|Val|Glu|Arg|Arg 485|Pro|Cys|Phe|Ser|Ala 490|Leu|Thr|Val|Asp|Glu 495|Thr|
|Tyr|Val|Pro|Lys 500|Glu|Phe|Lys|Ala|Glu 505|Thr|Phe|Thr|Phe|His 510|Ser|Asp|
|Ile|Cys|Thr 515|Leu|Pro|Asp|Lys|Glu 520|Lys|Gln|Ile|Lys|Lys 525|Gln|Thr|Ala|
|Leu|Ala|Glu 530|Leu|Val|Lys|His|Lys 535|Pro|Lys|Ala|Thr|Glu 540|Asp|Gln|Leu|

| Lys | Thr | Val | Met | Gly | Asp | Phe | Ala | Gln | Phe | Val | Asp | Lys | Cys | Cys | Lys |
| 545 | | | | 550 | | | | | 555 | | | | | | 560 |

| Ala | Ala | Asp | Lys | Asp | Asn | Cys | Phe | Ala | Thr | Glu | Gly | Pro | Asn | Leu | Val |
| | | | 565 | | | | | 570 | | | | | | 575 | |

| Ala | Arg | Ser | Lys | Glu | Ala | Leu | Ala |
| | | | 580 | | | | |

( 2 ) INFORMATION FOR SEQ ID NO:8:

( i ) SEQUENCE CHARACTERISTICS:
        ( A ) LENGTH: 579 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

| Val | Asp | His | His | Lys | His | Ile | Ala | Asp | Met | Tyr | Asn | Leu | Leu | Thr | Glu |
| 1 | | | | 5 | | | | | 10 | | | | | 15 | |

| Arg | Thr | Phe | Lys | Gly | Leu | Thr | Leu | Ala | Ile | Val | Ser | Gln | Asn | Leu | Gln |
| | | | 20 | | | | | 25 | | | | | 30 | | |

| Lys | Cys | Ser | Leu | Glu | Glu | Leu | Ser | Lys | Leu | Val | Asn | Glu | Ile | Asn | Asp |
| | | 35 | | | | | 40 | | | | | 45 | | | |

| Phe | Ala | Lys | Ser | Cys | Thr | Gly | Asn | Asp | Lys | Thr | Pro | Glu | Cys | Glu | Lys |
| | 50 | | | | | 55 | | | | | 60 | | | | |

| Pro | Ile | Gly | Thr | Leu | Phe | Tyr | Asp | Lys | Leu | Cys | Ala | Asp | Pro | Lys | Val |
| 65 | | | | | 70 | | | | | 75 | | | | | 80 |

| Gly | Val | Asn | Tyr | Glu | Trp | Ser | Lys | Glu | Cys | Cys | Ser | Lys | Gln | Asp | Pro |
| | | | | 85 | | | | | 90 | | | | | 95 | |

| Glu | Arg | Ala | Gln | Cys | Phe | Arg | Ala | His | Arg | Val | Phe | Glu | His | Asn | Pro |
| | | | 100 | | | | | 105 | | | | | 110 | | |

| Val | Arg | Pro | Lys | Pro | Glu | Glu | Thr | Cys | Ala | Leu | Phe | Lys | Glu | His | Pro |
| | | 115 | | | | | 120 | | | | | 125 | | | |

| Asp | Asp | Leu | Leu | Ser | Ala | Phe | Ile | His | Glu | Glu | Ala | Arg | Asn | His | Pro |
| | 130 | | | | | 135 | | | | | 140 | | | | |

| Asp | Leu | Tyr | Pro | Pro | Ala | Val | Leu | Leu | Leu | Thr | Gln | Gln | Tyr | Gly | Lys |
| 145 | | | | | 150 | | | | | 155 | | | | | 160 |

| Leu | Val | Glu | His | Cys | Cys | Glu | Glu | Glu | Asp | Lys | Asp | Lys | Cys | Phe | Ala |
| | | | | 165 | | | | | 170 | | | | | 175 | |

| Glu | Lys | Met | Lys | Glu | Leu | Met | Lys | His | Ser | His | Ser | Ile | Glu | Asp | Lys |
| | | | 180 | | | | | 185 | | | | | 190 | | |

| Gln | Lys | His | Phe | Cys | Trp | Ile | Val | Asn | Asn | Tyr | Pro | Glu | Arg | Val | Ile |
| | | 195 | | | | | 200 | | | | | 205 | | | |

| Lys | Ala | Leu | Asn | Leu | Ala | Arg | Val | Ser | His | Arg | Tyr | Pro | Lys | Pro | Asp |
| | 210 | | | | | 215 | | | | | 220 | | | | |

| Phe | Lys | Leu | Ala | His | Lys | Phe | Thr | Glu | Glu | Thr | Thr | His | Phe | Ile | Lys |
| 225 | | | | | 230 | | | | | 235 | | | | | 240 |

| Asp | Cys | Cys | His | Gly | Asp | Met | Phe | Glu | Cys | Met | Thr | Glu | Arg | Leu | Glu |
| | | | | 245 | | | | | 250 | | | | | 255 | |

| Leu | Ser | Glu | His | Thr | Cys | Gln | His | Lys | Asp | Glu | Leu | Ser | Thr | Lys | Leu |
| | | | 260 | | | | | 265 | | | | | 270 | | |

| Glu | Lys | Cys | Cys | Asn | Leu | Pro | Leu | Leu | Glu | Arg | Thr | Tyr | Cys | Ile | Val |

|   |   |   |   |   | 275 |   |   |   |   | 280 |   |   |   |   | 285 |   |   |   |
|---|---|---|---|---|---|---|---|---|---|---|---|---|---|---|---|---|---|---|
| Thr | Leu | Glu | Asn | Asp | Val | Pro | Ala | Glu | Leu | Ser | Lys | Pro | Ile | Thr |
| | | | | 290 | | | | | 295 | | | | | 300 | | | | |
| Glu | Phe | Thr | Glu | Asp | Pro | His | Val | Cys | Gln | Lys | Tyr | Ala | Glu | Asn | Lys |
| 305 | | | | | 310 | | | | | 315 | | | | | 320 |
| Ser | Phe | Leu | Glu | Ile | Ser | Pro | Trp | Gln | Ser | Gln | Glu | Thr | Pro | Glu | Leu |
| | | | | 325 | | | | | 330 | | | | | 335 | |
| Ser | Glu | Gln | Phe | Leu | Leu | Gln | Ser | Ala | Lys | Glu | Tyr | Glu | Ser | Leu | Leu |
| | | | 340 | | | | | 345 | | | | | 350 | | |
| Asn | Lys | Cys | Cys | Phe | Ser | Asp | Asn | Pro | Pro | Glu | Cys | Tyr | Lys | Asp | Gly |
| | | 355 | | | | | 360 | | | | | 365 | | | |
| Ala | Asp | Arg | Phe | Met | Asn | Glu | Ala | Lys | Glu | Arg | Phe | Ala | Tyr | Leu | Lys |
| | 370 | | | | | 375 | | | | | 380 | | | | |
| Gln | Asn | Cys | Asp | Ile | Leu | His | Glu | His | Gly | Glu | Tyr | Leu | Phe | Glu | Asn |
| 385 | | | | | 390 | | | | | 395 | | | | | 400 |
| Glu | Leu | Leu | Ile | Arg | Tyr | Thr | Lys | Lys | Met | Pro | Gln | Val | Ser | Asp | Glu |
| | | | | 405 | | | | | 410 | | | | | 415 | |
| Thr | Leu | Ile | Gly | Ile | Ala | His | Gln | Met | Ala | Asp | Ile | Gly | Glu | His | Cys |
| | | | 420 | | | | | 425 | | | | | 430 | | |
| Cys | Ala | Val | Pro | Glu | Asn | Gln | Arg | Met | Pro | Cys | Ala | Glu | Gly | Asp | Leu |
| | | 435 | | | | | 440 | | | | | 445 | | | |
| Thr | Ile | Leu | Ile | Gly | Lys | Met | Cys | Glu | Arg | Gln | Lys | Lys | Thr | Phe | Ile |
| | 450 | | | | | 455 | | | | | 460 | | | | |
| Asn | Asn | His | Val | Ala | His | Cys | Cys | Thr | Asp | Ser | Tyr | Ser | Gly | Met | Arg |
| 465 | | | | | 470 | | | | | 475 | | | | | 480 |
| Ser | Cys | Phe | Thr | Ala | Leu | Gly | Pro | Asp | Glu | Asp | Tyr | Val | Pro | Pro | Pro |
| | | | | 485 | | | | | 490 | | | | | 495 | |
| Val | Thr | Asp | Asp | Thr | Phe | His | Phe | Asp | Lys | Ile | Cys | Thr | Ala | Asn |
| | | | 500 | | | | | 505 | | | | | 510 | | |
| Asp | Lys | Glu | Lys | Gln | His | Ile | Lys | Gln | Lys | Phe | Leu | Val | Lys | Leu | Ile |
| | | 515 | | | | | 520 | | | | | 525 | | | |
| Lys | Val | Ser | Pro | Lys | Leu | Glu | Lys | Asn | His | Ile | Asp | Glu | Trp | Leu | Leu |
| | 530 | | | | | 535 | | | | | 540 | | | | |
| Glu | Phe | Leu | Lys | Met | Val | Gln | Lys | Cys | Cys | Thr | Ala | Asp | Glu | His | Gln |
| 545 | | | | | 550 | | | | | 555 | | | | | 560 |
| Pro | Cys | Phe | Asp | Thr | Glu | Lys | Pro | Val | Leu | Ile | Glu | His | Cys | Gln | Lys |
| | | | | 565 | | | | | 570 | | | | | 575 | |
| Leu | His | Pro |

( 2 ) INFORMATION FOR SEQ ID NO:9:

( i ) SEQUENCE CHARACTERISTICS:
        ( A ) LENGTH: 590 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:9:

| Ser | Gln | Ala | Gln | Asn | Gln | Ile | Cys | Thr | Ile | Phe | Thr | Glu | Ala | Lys | Glu |
|---|---|---|---|---|---|---|---|---|---|---|---|---|---|---|---|
| 1 | | | | 5 | | | | | 10 | | | | | 15 | |
| Asp | Gly | Phe | Lys | Ser | Leu | Ile | Leu | Val | Gly | Leu | Ala | Gln | Asn | Leu | Pro |

-continued

|  |  |  | 20 |  |  |  | 25 |  |  |  | 30 |  |  |  |
|---|---|---|---|---|---|---|---|---|---|---|---|---|---|---|
| Asp | Ser | Thr 35 | Leu | Gly | Asp | Leu 40 | Val | Pro | Leu | Ile | Ala 45 | Glu | Ala | Leu | Ala |
| Met | Gly 50 | Val | Lys | Cys | Cys 55 | Ser | Asp | Thr | Pro | Pro 60 | Glu | Asp | Cys | Glu | Arg |
| Asp 65 | Val | Ala | Asp | Leu | Phe 70 | Gln | Ser | Ala | Val | Cys 75 | Ser | Ser | Glu | Thr | Leu 80 |
| Val | Glu | Lys | Asn | Asp 85 | Leu | Lys | Met | Cys | Cys 90 | Glu | Lys | Thr | Ala | Ala 95 | Glu |
| Arg | Thr | His | Cys 100 | Phe | Val | Asp | His | Lys 105 | Ala | Lys | Ile | Pro | Arg 110 | Asp | Leu |
| Ser | Leu | Lys 115 | Ala | Glu | Leu | Pro | Ala 120 | Ala | Asp | Gln | Cys | Glu 125 | Asp | Phe | Lys |
| Lys | Asp 130 | His | Lys | Ala | Phe | Val 135 | Gly | Arg | Phe | Ile | Phe 140 | Lys | Phe | Ser | Lys |
| Ser 145 | Asn | Pro | Met | Leu | Pro 150 | Pro | His | Val | Val | Leu 155 | Ala | Ile | Ala | Lys | Gly 160 |
| Tyr | Gly | Glu | Val | Leu 165 | Thr | Thr | Cys | Cys | Glu 170 | Ala | Glu | Ala | Gln 175 | Thr |  |
| Cys | Phe | Asp | Thr 180 | Lys | Lys | Ala | Thr | Phe 185 | Gln | His | Ala | Val | Met 190 | Lys | Arg |
| Val | Ala | Glu 195 | Leu | Arg | Ser | Leu | Cys 200 | Ile | Val | His | Lys | Lys 205 | Tyr | Gly | Asp |
| Arg | Val 210 | Val | Lys | Ala | Lys | Lys 215 | Leu | Val | Gln | Tyr | Ser 220 | Gln | Lys | Met | Pro |
| Gln 225 | Ala | Ser | Phe | Gln | Glu 230 | Met | Gly | Gly | Met | Val 235 | Asp | Lys | Ile | Val | Ala 240 |
| Thr | Val | Ala | Pro | Cys 245 | Cys | Ser | Gly | Asp | Met 250 | Val | Thr | Cys | Met | Lys 255 | Glu |
| Arg | Lys | Thr | Leu 260 | Val | Asp | Glu | Val | Cys 265 | Ala | Asp | Glu | Ser | Val 270 | Leu | Ser |
| Arg | Ala | Ala 275 | Gly | Leu | Ser | Ala | Cys 280 | Cys | Lys | Glu | Asp | Ala 285 | Val | His | Arg |
| Gly | Ser 290 | Cys | Val | Glu | Ala | Met 295 | Lys | Pro | Asp | Pro | Lys 300 | Pro | Asp | Gly | Leu |
| Ser 305 | Glu | His | Tyr | Asp | Ile 310 | His | Ala | Asp | Ile | Ala 315 | Ala | Val | Cys | Gln | Thr 320 |
| Phe | Thr | Lys | Pro | Thr 325 | Asp | Val | Ala | Met | Gly 330 | Lys | Leu | Val | Tyr | Glu 335 | Ile |
| Ser | Val | Arg | His 340 | Pro | Glu | Ser | Ser | Gln 345 | Gln | Val | Ile | Leu | Arg 350 | Phe | Ala |
| Lys | Glu | Ala 355 | Glu | Gln | Ala | Leu | Leu 360 | Gln | Cys | Cys | Asp | Met 365 | Glu | Asp | His |
| Ala | Glu | Cys 370 | Val | Lys | Thr | Ala | Leu 375 | Ala | Gly | Ser | Asp | Ile 380 | Asp | Lys | Lys |
| Ile 385 | Thr | Asp | Glu | Thr | Asp 390 | Tyr | Tyr | Lys | Lys | Met 395 | Cys | Ala | Ala | Glu | Ala 400 |
| Ala | Val | Ser | Asp | Asp 405 | Ser | Phe | Glu | Lys | Ser 410 | Met | Met | Val | Tyr | Tyr 415 | Thr |
| Arg | Ile | Met | Pro 420 | Gln | Ala | Ser | Phe | Asp 425 | Gln | Leu | His | Met | Val 430 | Ser | Gln |
| Thr | Val | His 435 | Asp | Val | Leu | His | Ala 440 | Cys | Cys | Lys | Asp | Glu 445 | Gln | Gly | His |

-continued

| Phe | Val 450 | Leu | Pro | Cys | Ala | Glu 455 | Glu | Lys | Leu | Thr | Asp 460 | Ala | Ile | Asp | Ala |
|---|---|---|---|---|---|---|---|---|---|---|---|---|---|---|---|
| Thr 465 | Cys | Asp | Asp | Tyr | Asp 470 | Pro | Ser | Ser | Ile | Asn 475 | Pro | His | Ile | Ala | His 480 |
| Cys | Cys | Asn | Gln | Ser 485 | Tyr | Ser | Met | Arg | Arg 490 | His | Cys | Ile | Leu | Ala 495 | Ile |
| Gln | Pro | Asp | Thr 500 | Glu | Phe | Thr | Pro | Pro 505 | Glu | Leu | Asp | Ala | Ser 510 | Ser | Phe |
| His | Met | Gly 515 | Pro | Glu | Leu | Cys | Thr 520 | Lys | Asp | Ser | Lys | Asp 525 | Leu | Leu | Leu |
| Ser | Gly 530 | Lys | Lys | Leu | Leu | Tyr 535 | Gly | Val | Val | Arg | His 540 | Lys | Thr | Thr | Ile |
| Thr 545 | Glu | Asp | His | Leu | Lys 550 | Thr | Ile | Ser | Thr | Lys 555 | Tyr | His | Thr | Met | Lys 560 |
| Glu | Lys | Cys | Cys | Ala 565 | Ala | Glu | Asp | Gln | Ala 570 | Ala | Cys | Phe | Thr | Glu 575 | Glu |
| Ala | Pro | Lys | Leu 580 | Val | Ser | Glu | Ser | Ala 585 | Glu | Leu | Val | Lys | Val 590 | | |